United States Patent
Finlay et al.

(10) Patent No.: US 6,514,268 B2
(45) Date of Patent: *Feb. 4, 2003

(54) METHOD OF OPERATING MICROSURGICAL INSTRUMENTS

(75) Inventors: Russell L. Finlay, Dana Point, CA (US); William W. Furniss, Ranch Santa Margarita, CA (US); John C. Huculak, Mission Viejo, CA (US); Christopher C. Jung, Mission Viejo, CA (US)

(73) Assignee: Alcon Universal Ltd., Hunenberg (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/386,003

(22) Filed: Aug. 30, 1999

(65) Prior Publication Data

US 2002/0173814 A1 Nov. 21, 2002

(51) Int. Cl.$^7$ ................................................ A61B 17/32
(52) U.S. Cl. ............................................................ 606/170
(58) Field of Search ............................ 604/22; 606/107, 606/167, 168, 170, 171, 180

(56) References Cited

U.S. PATENT DOCUMENTS

| | | | |
|---|---|---|---|
| 3,884,238 A | | 5/1975 | O'Malley et al. ............ 128/305 |
| 4,493,698 A | * | 1/1985 | Wang et al. ................. 604/119 |
| 4,577,629 A | | 3/1986 | Martinez ..................... 128/305 |
| 4,696,298 A | | 9/1987 | Higgins et al. .............. 128/305 |
| 4,757,814 A | | 7/1988 | Wang et al. ................. 128/318 |
| 4,819,635 A | | 4/1989 | Shapiro ....................... 128/305 |
| 4,841,984 A | * | 6/1989 | Armeniades et al. ........ 600/561 |
| 4,909,249 A | | 3/1990 | Akkas et al. ................. 606/107 |
| 4,940,468 A | | 7/1990 | Petillo ......................... 606/170 |
| 4,986,827 A | | 1/1991 | Akkas et al. ................. 606/107 |
| 5,019,035 A | | 5/1991 | Missirlian et al. ............ 604/22 |
| 5,020,535 A | * | 6/1991 | Parker et al. ................ 606/107 |
| 5,024,652 A | * | 6/1991 | Dumenek et al. ............. 604/22 |
| 5,047,008 A | | 9/1991 | de Juan, Jr. et al. .......... 604/22 |
| 5,059,204 A | | 10/1991 | Lawson et al. .............. 606/171 |
| 5,061,238 A | | 10/1991 | Shuler ......................... 604/22 |
| 5,176,628 A | | 1/1993 | Charles et al. ................ 604/22 |
| 5,284,472 A | | 2/1994 | Sussman et al. .............. 604/22 |
| 5,354,268 A | | 10/1994 | Peterson et al. .............. 604/35 |
| 5,380,280 A | | 1/1995 | Peterson ....................... 604/65 |
| 5,423,844 A | | 6/1995 | Miller ......................... 606/171 |
| 5,474,532 A | | 12/1995 | Steppe ......................... 604/22 |
| 5,520,652 A | | 5/1996 | Peterson ...................... 604/119 |
| 5,630,827 A | | 5/1997 | Vijfvinkel ................... 606/171 |
| 5,674,194 A | | 10/1997 | Jung et al. .................... 604/65 |
| 5,733,297 A | | 3/1998 | Wang .......................... 606/167 |
| 5,782,849 A | | 7/1998 | Miller ......................... 606/159 |
| 5,833,643 A | | 11/1998 | Ross et al. .................... 604/22 |
| 6,010,496 A | | 1/2000 | Appelbaum et al. ........... 606/4 |

* cited by examiner

Primary Examiner—Michael J. Milano
Assistant Examiner—Vy Q. Bui
(74) Attorney, Agent, or Firm—W. David Lee

(57) ABSTRACT

A method of operating a microsurgical instrument, such as a vitrectomy probe, is disclosed. The probe includes a port for receiving tissue and an inner cutting member. A flow of tissue is induced into the port with a vacuum source, and the member is actuated in a cyclic manner to open and close the port over a plurality of cut rates. A duty cycle of the member is varied with the cut rate to vary the flow of the tissue into the port. The method yields the ability to adjust flow rate into the probe and aperture of the probe for a given cut rate so as to effectively perform a wide variety of vitreoretinal surgical objectives.

1 Claim, 7 Drawing Sheets

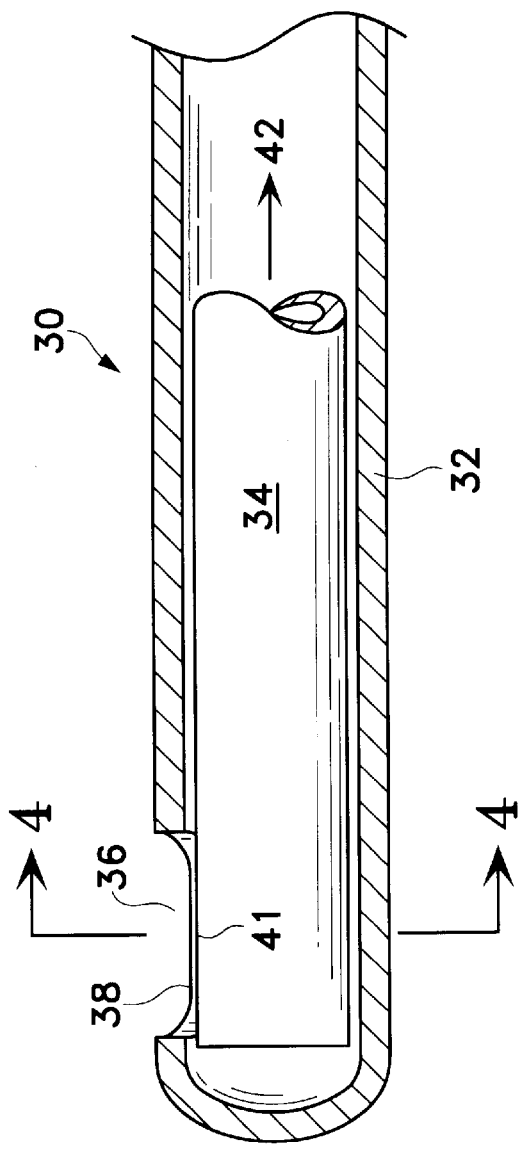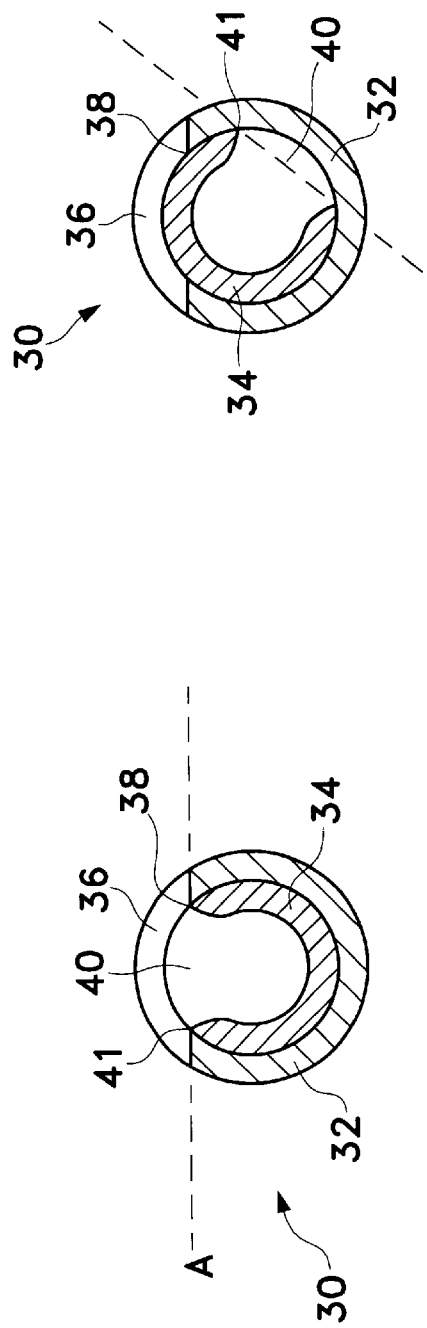

METHOD OF OPERATING MICROSURGICAL INSTRUMENTS

FIELD OF THE INVENTION

The present invention generally pertains to a method of operating microsurgical instruments. More particularly, but not by way of limitation, the present invention pertains to a method of operating microsurgical instruments used in posterior segment ophthalmic surgery, such as vitrectomy probes, so as to optimize the performance of the instruments for a variety of surgical objectives.

DESCRIPTION OF THE RELATED ART

Many microsurgical procedures require precision cutting and/or removal of various body tissues. For example, certain ophthalmic surgical procedures require the cutting and/or removal of the vitreous humor, a transparent jelly-like material that fills the posterior segment of the eye. The vitreous humor, or vitreous, is composed of numerous microscopic fibers that are often attached to the retina. Therefore, cutting and removal of the vitreous must be done with great care to avoid traction on the retina, the separation of the retina from the choroid, a retinal tear, or, in the worst case, cutting and removal of the retina itself.

The use of microsurgical cutting probes in posterior segment ophthalmic surgery is well known. Such vitrectomy probes are typically inserted via an incision in the sclera near the pars plana. The surgeon may also insert other microsurgical instruments such as a fiber optic illuminator, an infusion cannula, or an aspiration probe during the posterior segment surgery. The surgeon performs the procedure while viewing the eye under a microscope.

Conventional vitrectomy probes typically include a hollow outer cutting member, a hollow inner cutting member arranged coaxially with and movably disposed within the hollow outer cutting member, and a port extending radially through the outer cutting member near the distal end thereof. Vitreous humor is aspirated into the open port, and the inner member is actuated, closing the port. Upon the closing of the port, cutting surfaces on both the inner and outer cutting members cooperate to cut the vitreous, and the cut vitreous is then aspirated away through the inner cutting member. U.S. Pat. No. 4,577,629 (Martinez); U.S. Pat. No. 5,019,035 (Missirlian et al.); U.S. Pat. No. 4,909,249 (Akkas et al.); U.S. Pat. No. 5,176,628 (Charles et al.); U.S. Pat. No. 5,047,008 (de Juan et al.); U.S. Pat. No. 4,696,298 (Higgins et al.); and U.S. Pat. No. 5,733,297 (Wang) all disclose various types of vitrectomy probes, and each of these patents is incorporated herein in its entirety by reference.

Conventional vitrectomy probes include "guillotine style" probes and rotational probes. A guillotine style probe has an inner cutting member that reciprocates along its longitudinal axis. A rotational probe has an inner cutting member that reciprocates around its longitudinal axis. In both types of probes, the inner cutting members are actuated using various methods. For example, the inner cutting member can be moved from the open port position to the closed port position by pneumatic pressure against a piston or diaphragm assembly that overcomes a mechanical spring. Upon removal of the pneumatic pressure, the spring returns the inner cutting member from the closed port position to the open port position. As another example, the inner cutting member can be moved from the open port position to the closed port position using a first source of pneumatic pressure, and then can be moved from the closed port position to the open port position using a second source of pneumatic pressure. As a further example, the inner cutting member can be electromechanically actuated between the open and closed port positions using a conventional rotating electric motor or a solenoid. U.S. Pat. No. 4,577,629 provides an example of a guillotine style, pneumatic piston/mechanical spring actuated probe. U.S. Pat. Nos. 4,909,249 and 5,019,035 disclose guillotine style, pneumatic diaphragm/mechanical spring actuated probes. U.S. Pat. No. 5,176,628 shows a rotational dual pneumatic drive probe.

With each of the above-described conventional vitrectomy probes, the inner cutting member is always actuated from a fully open port position, to a fully closed port position, and back to a fully open port position. It is believed that certain conventional guillotine style, pneumatic/mechanical spring actuated probes are physically capable of being operated at cutting speeds that do not allow the port to return to its fully open position in each cut cycle. However, the surgical systems with which such probes have been operated have not allowed this mode of operation to occur. This is because the ophthalmic surgical community has historically believed that a fully open port is critical to maximize fluid flow into and inclusion of vitreous within the port and to expedite vitreous cutting and removal.

Most conventional probes are sized to have a relatively large fully open port size (e.g. 0.020 inches to 0.030 inches) for use in a variety of surgical objectives. Operating at relatively low cut rates (e.g. up to 800 cuts/minute), these probes may be used to remove large amounts of vitreous in a single cut cycle, such as in core vitrectomy, and to cut physically large vitreous tissue, such as traction bands. In addition, these probes are also used to perform more delicate operations such as mobile tissue management (e.g. removing vitreous near a detached portion of the retina or a retinal tear), vitreous base dissection, and membrane removal. However, the combined effect of large port size, large cut stroke, and relatively slow cut rate of these probes sometimes creates unwanted turbulence of the vitreous and retinal tissues and a large peak to peak fluctuation of intraocular pressure within the eye. Both of these limitations cause difficulty for the surgeon and can be detrimental to the patient.

Specialized vitrectomy probes have been developed. For example, probes with relatively smaller fully open port sizes (e.g. 0.010 inches) have been used to perform more delicate surgical objectives near the retina. An example of such a specialized probe is the Microport® probe available from Alcon Laboratories, Inc. of Fort Worth, Tex. However, these probes are not highly effective for core vitrectomy, and thus the surgeon is often forced to use and repeatedly insert multiple vitrectomy probes within a patient's eye, complicating the surgery and increasing trauma to the patient. As another example, U.S. Pat. Nos. 4,909,249 and 5,019,035 disclose probes with manually adjustable port sizes. However, repeated manual adjustment of port size is time consuming and awkward. Relatively high cut rate probes have been developed by Storz Instrument Company of St. Louis (the "Lightning" probe) and Scieran Technologies, Inc. of Laguna Hills, Calif. (the "Vit Commander" probe). However, it is believed that these probes are somewhat limited in flow rate, rendering them less effective for core vitrectomy.

Therefore, a need exists for an improved method of performing all of the fundamental aspects of vitrectomy surgery—core vitrectomy, mobile tissue management, vitreous base dissection, and membrane removal—that does not suffer from the above-described limitations. As is explained in greater detail hereinbelow, this method would automatically control cut rate, port open duty cycle, and port open size or aperture as needed during a procedure to achieve a broad range of surgical objectives. An improved method is also needed for operating microsurgical instruments other than vitrectomy probes. Ideally, the improved methods would be safe for the patient, easy for the surgeon to use, and economically feasible.

SUMMARY OF THE INVENTION

One aspect of the present invention comprises a method of operating a microsurgical instrument. The microsurgical instrument includes a port for receiving tissue and a member. A flow of tissue is induced into the port with a vacuum source, and the member is actuated in a cyclic manner to open and close the port over a plurality of cycle rates. A duty cycle of the member is varied with the cycle rate to vary the flow of the tissue into the port.

The microsurgical instrument may comprise a vitrectomy probe, an aspiration probe, or other cutting probe. In the vitrectomy probe embodiment, the present invention yields the ability to adjust flow rate into the probe and aperture of the probe for a given cut rate so as to effectively perform a wide variety of vitreoretinal surgical objectives.

BRIEF DESCRIPTION OF THE DRAWINGS

For a more complete understanding of the present invention, and for further objects and advantages thereof, reference is made to the following description taken in conjunction with the accompanying drawings in which:

FIG. 3 is a side, partially sectional view of a second vitrectomy probe preferred for use in the method of the present invention shown in a fully open port position;

FIG. 4 is a cross-sectional view of the probe of FIG. 3 along line 4—4;

FIG. 5 is a cross-sectional view of the probe of FIG. 3 along line 4—4 shown in a closed port position;

DETAILED DESCRIPTION OF PREFERRED EMBODIMENTS

The preferred embodiments of the present invention and their advantages are best understood by referring to FIGS. 1 through 12 of the drawings, like numerals being used for like and corresponding parts of the various drawings.

Figure 1:
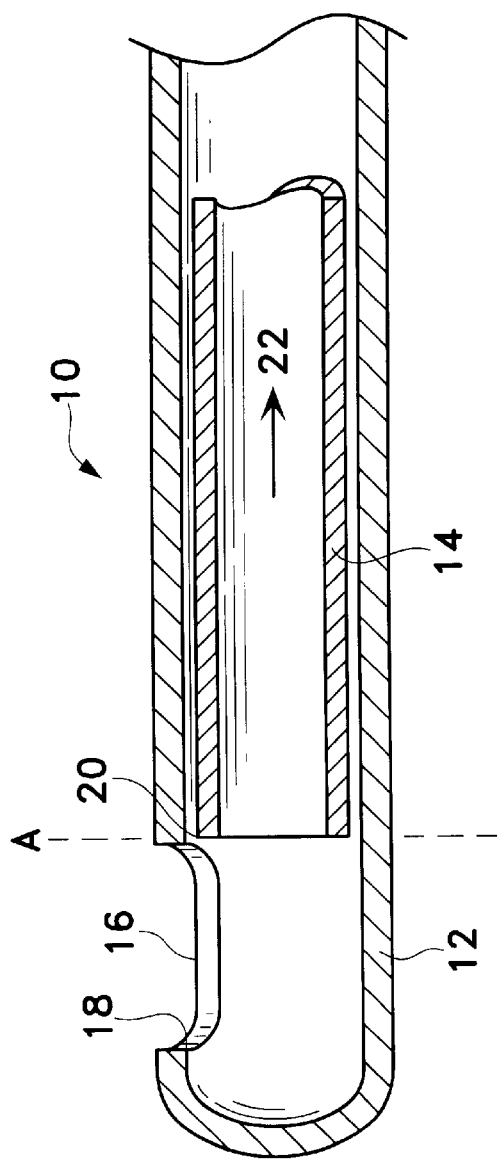
FIG. 1 is a side sectional view of a first vitrectomy probe preferred for use in the method of the present invention shown in the fully open port position.
Figure 2:
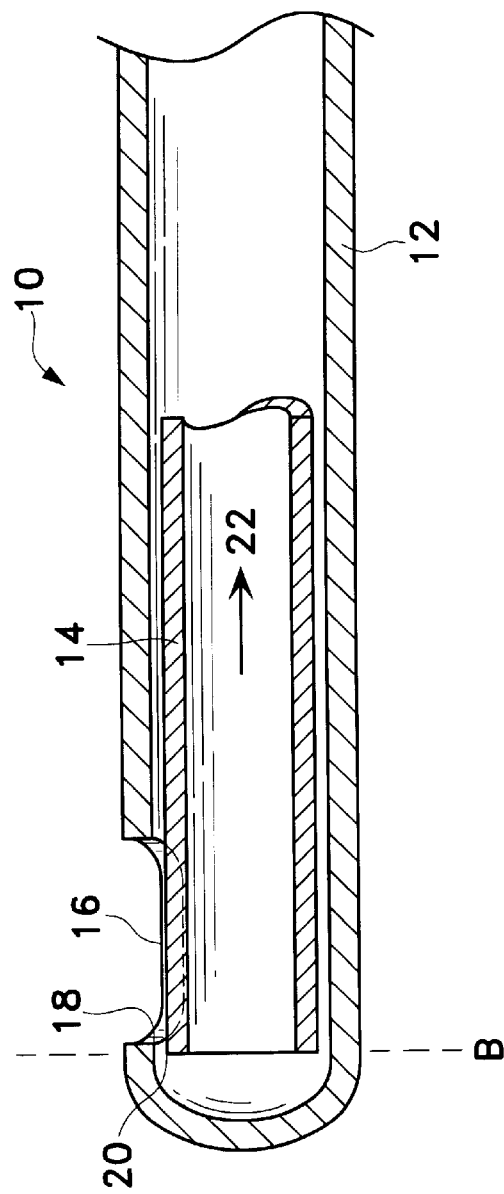
FIG. 2 is a side sectional view of the probe of FIG. 1 shown in a closed port position.

Referring first to FIGS. 1 and 2, a distal end of a microsurgical instrument 10 is schematically illustrated. Microsurgical instrument 10 is preferably a guillotine style vitrectomy probe and includes a tubular outer cutting member 12 and a tubular inner cutting member 14 movably disposed within outer cutting member 12. Outer cutting member 12 has a port 16 and a cutting edge 18. Port 16 preferably has a length of about 0.020 inches along the longitudinal axis of probe 10. Inner cutting member 14 has a cutting edge 20.

During operation of probe 10, inner cutting member 14 is moved along the longitudinal axis of probe 10 from a position A as shown in FIG. 1, to a position B as shown in FIG. 2, and then back to position A in a single cut cycle. Position A corresponds to a fully open position of port 16, and position B corresponds to a fully closed position of port 16. In position A, vitreous humor or other tissue is aspirated into port 16 and within inner cutting member 14 by vacuum induced fluid flow represented by arrow 22. In position B, the vitreous within port 16 and inner cutting member 14 is cut or severed by cutting edges 18 and 20 and is aspirated away by vacuum induced fluid flow 22. Cutting edges 18 and 20 are preferably formed in an interference fit to insure cutting of the vitreous. In addition, positions A and B are conventionally located somewhat outside the ends of port 16 to account for variations in the actuation of inner cutting member 14 in specific probes 10.

Referring now to FIGS. 3 through 5, a distal end of a microsurgical instrument 30 is schematically illustrated. Instrument 30 is preferably a rotational vitrectomy probe and includes a tubular outer cutting member 32 and a tubular inner cutting member 34 movably disposed within outer cutting member 32. Outer cutting member 32 has a port 36 and a cutting edge 38. Port 36 preferably has a length of about 0.020 inches along the longitudinal axis of probe 30. Inner cutting member 34 has an opening 40 having a cutting edge 41.

During operation of probe 30, inner cutting member 34 is rotated about the longitudinal axis of probe 30 from a position A as shown in FIG. 4, to a position B as shown in FIG. 5, and then back to position A in a single cut cycle. Position A corresponds to a fully open position of port 36, and position B corresponds to a fully closed position of port 36. In position A, vitreous humor or other tissue is aspirated into port 36, opening 40, and inner cutting member 34 by vacuum induced fluid flow represented by arrow 42. In position B, the vitreous within inner cutting member 34 is cut or severed by cutting edges 38 and 41 and is aspirated away by vacuum induced flow 42. Cutting edges 38 and 41 are preferably formed in an interference fit to insure cutting of the vitreous. In addition, position B is conventionally located somewhat past the edge of cutting surface 38 of outer cutting member 32 to account for variations in the actuation of inner cutting member 34 in specific probes 30.

Inner cutting member 14 of probe 10 is preferably moved from the open port position to the closed port position by application of pneumatic pressure against a piston or diaphragm assembly that overcomes a mechanical spring. Upon removal of the pneumatic pressure, the spring returns inner cutting member 14 from the closed port position to the open port position. Inner cutting member 34 of probe 20 is preferably moved from the open port position to the closed port position using a first source of pneumatic pressure, and then moved from the closed port position to the open port position using a second source of pneumatic pressure. The first source of pneumatic pressure is pulsed, and the second source of pneumatic pressure may be pulsed or fixed. Alternatively, inner cutting members 14 and 34 can be electromechanically actuated between their respective open and closed port positions using a conventional linear motor or solenoid. The implementation of certain ones of these actuation methods is more fully described in U.S. Pat. Nos. 4,577,629; 4,909,249; 5,019,035; and 5,176,628 mentioned above. For purposes of illustration and not by way of limitation, the method of the present invention will be described hereinafter with reference to a guillotine style, pneumatic/mechanical spring actuated vitrectomy probe 10.

Figure 6:
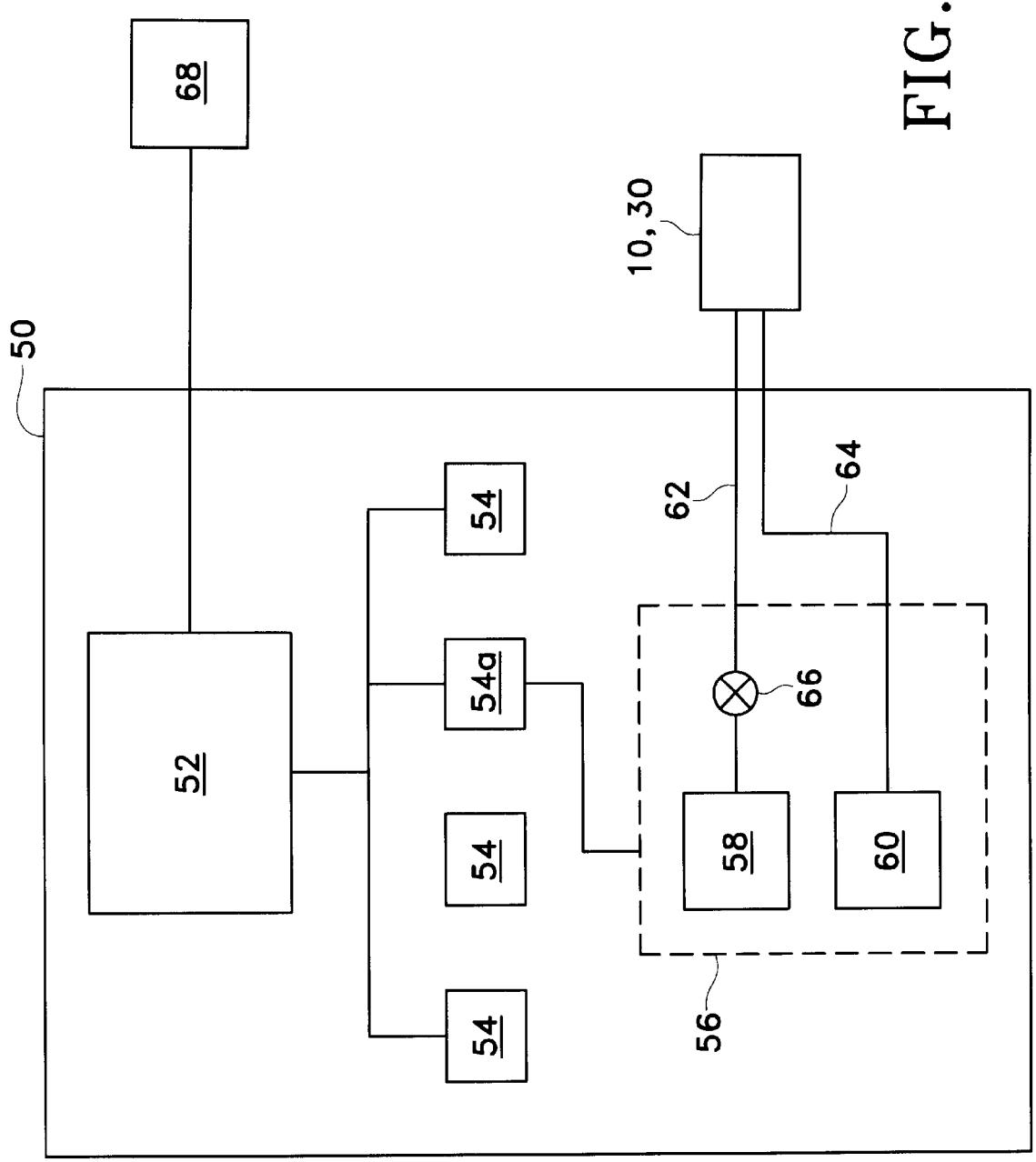
FIG. 6 is a block diagram of certain portions of a microsurgical system preferred for use in the method of the present invention.

FIG. 6 shows a block diagram of certain portions of the electronic and pneumatic sub-assemblies of a microsurgical system 50 preferred for use in the present invention. For example, system 50 could be the Accurus® surgical system sold by Alcon Laboratories, Inc. of Fort Worth, Tex. or another conventional ophthalmic microsurgical system. System 50 preferably includes a host microcomputer 52 that is electronically connected to a plurality of microcontrollers 54. Microcomputer 52 preferably comprises an Intel® 486™ microprocessor, and microcontrollers 54 preferably comprise Intel® 80C196™ microprocessors. Of course, other conventional microprocessors having equivalent or superior performance can be utilized for microcomputer 52 and microcontrollers 54, if desired. Microcontroller 54a is electronically connected with and controls an air/fluid module 56 of system 50. Air/fluid module 56 preferably includes a source of pneumatic pressure 58 and a source of vacuum 60, both of which are in fluid communication with probe 10 or probe 30 via conventional PVC tubing 62 and 64. Air/fluid module 56 also preferably includes appropriate electrical connections between its various components. Although both probes 10 and 30 may be used with system 50, the remainder of this description of system 50 will only reference probe 10 for ease of description.

Pneumatic pressure source 58 provides pneumatic drive pressure to probe 10, preferably at a pressure of about 57 psi. A solenoid valve 66 is disposed within tubing 62 between pneumatic pressure source 58 and probe 10. Solenoid valve 66 preferably has a response time of about 2 to about 3 milliseconds. System 50 also preferably includes a variable controller 68. Variable controller 68 is electronically connected with and controls solenoid valve 66 via microcomputer 52 and microcontroller 54a. As is later explained in greater detail, variable controller 68 preferably provides a variable electric signal that cycles solenoid valve 66 between open and closed positions so as to provide a cycled pneumatic pressure that drives inner cutting member 14 of probe 10 from its open port position to its closed port position at a variety of cut rates. Although not shown in FIG. 6, air/fluid module 56 may also include a second pneumatic pressure source and solenoid valve controlled by microcontroller 54a that drives inner cutting member 34 of probe 30 from its closed port position to its open port position. Variable controller 68 is preferably a conventional foot switch or foot pedal that is operable by a surgeon. For example, variable controller 68 may be the foot pedal sold as part of the Accurus® surgical system mentioned above. Alternatively, variable controller 68 could also be a conventional hand held switch or "touch screen" control, if desired.

Figure 7:
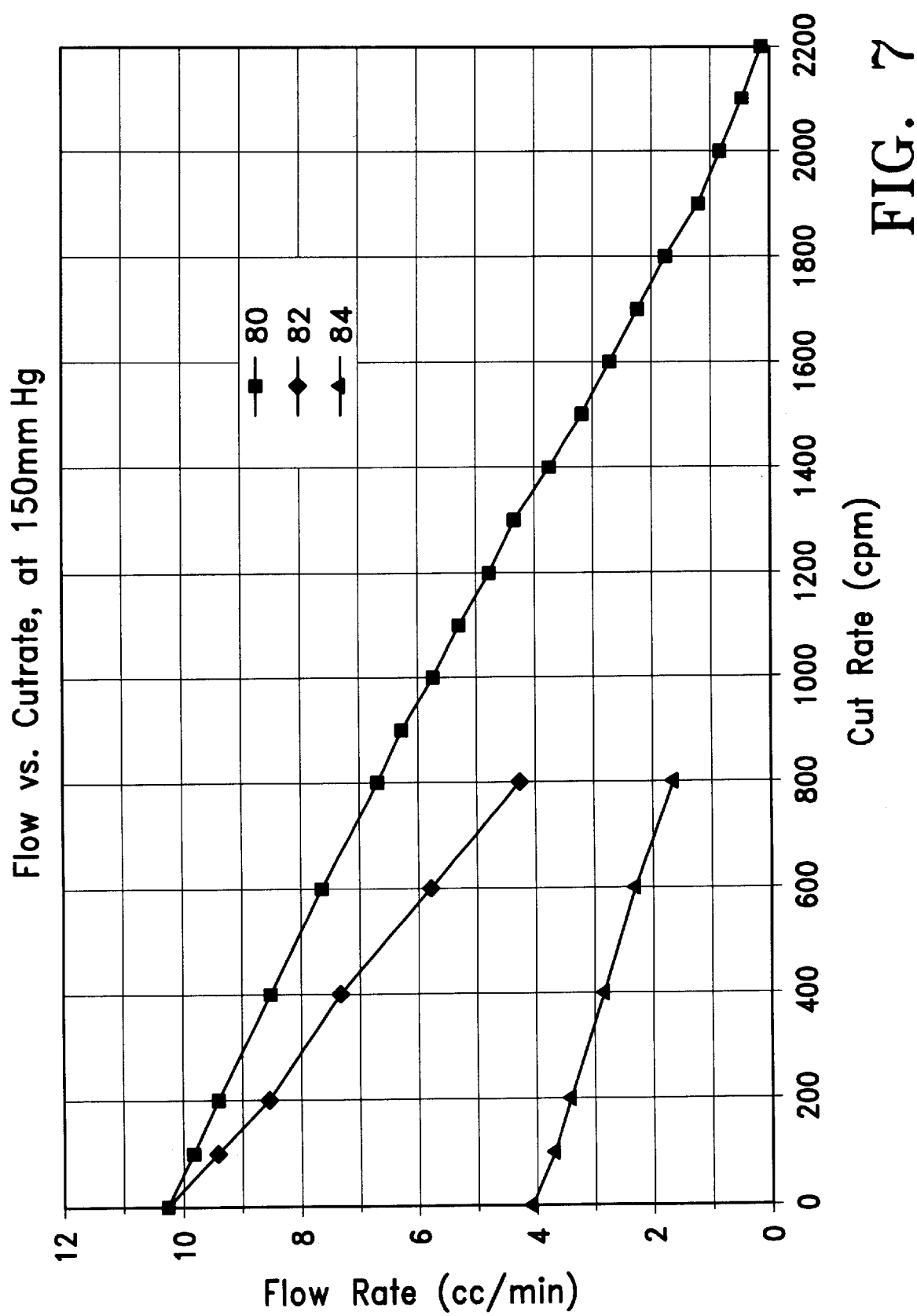
FIG. 7 shows a flow profile for the probe of FIG. 1 according to a preferred embodiment of the present invention compared to a conventional flow profile for the probe of FIG. 1 and a conventional flow profile for the Microport® probe.

FIG. 7 shows flow rate versus cut rate for three, exemplary vitrectomy probes. Profile 80 shows a preferred flow profile for a pneumatic/mechanical spring actuated probe 10 actuated according to the preferred method of the present invention. Profile 82 shows a conventional flow profile for a pneumatic/mechanical spring actuated probe 10. Profile 84 shows a conventional flow profile for the Microport® probe. As shown in FIG. 7, flow profile 80 is preferably substantially linear.

At constant aspiration of 150 mmHg vacuum, flow profile 84 is approximately 40% that of profile 82 at all cut rates. Although the probe of profile 84 achieves the 1–2 cc/min flow rates that are desired by the ophthalmic surgical community when performing delicate retinal work, this same probe cannot achieve the higher 8–10 cc/min flow rates that are called for when performing core vitrectomy.

FIG. 7 reveals a ratio of 0 cpm (cuts/minute) vs. maximum cpm flow of approximately 2.5:1 for each of profiles 82 and 84. In contrast, the flow ratio for profile 80 is greater than 50:1. By using the method of the present invention to modulate flow through probe 10 more completely by the application of various cut rates, port open duty cycles, and port apertures, flow profile 80 well exceeds that of profiles 82 and 84 combined. Such improved range of flow greatly reduces or eliminates the need for insertion of multiple probes into a patient's eye for different surgical objectives, reduces the complexity of the surgery, and reduces the associated trauma to the patient.

Figure 8:
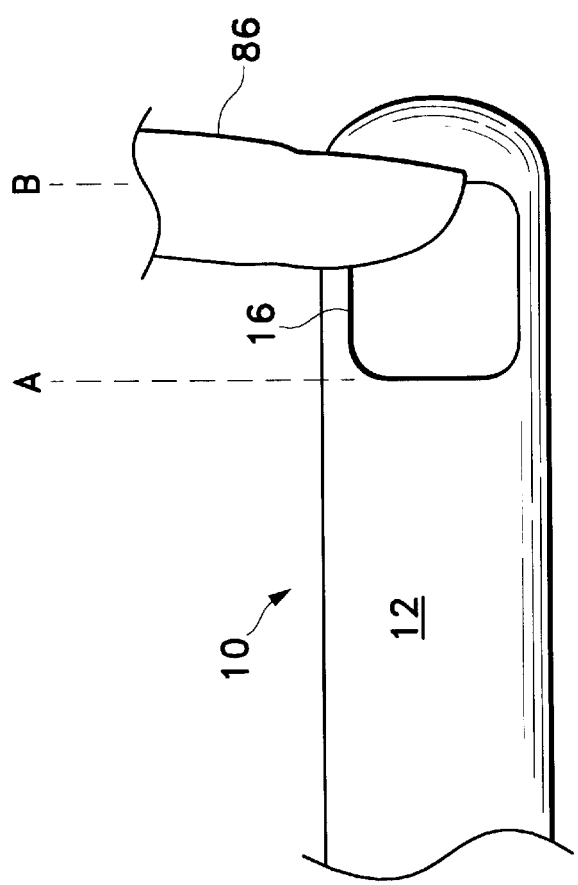
FIGS. 8 and 9 are top views of the probe of FIG. 1 illustrating the ability to vary open port size with the size of tissue to be cut and aspirated according to a preferred method of the present invention.
Figure 9:
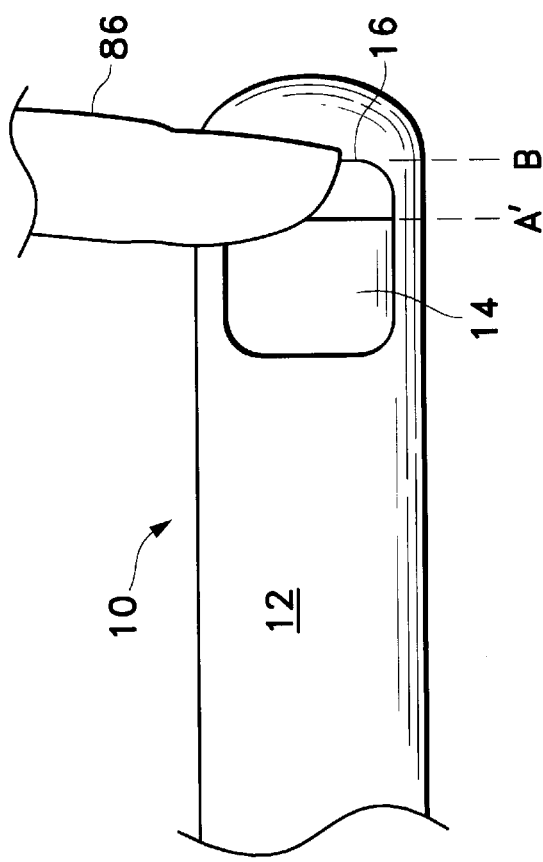

The improved performance of probe 10 in flow profile 80 is achieved by dynamically varying the port open duty cycle of the probe with cut rate. At high cut rates, such variation of the duty cycle also facilitates the variation of the "open" size or aperture of port 16. One of the important discoveries of the present invention is that it is preferable to vary the open size of port 16 according to the size of the vitreous or other tissue targeted for cutting and removal. For example, FIG. 8 shows inner cutting member 14 of probe 10 being actuated from a fully open position A of port 16, to a fully closed port position B, and back to a position A in a single cut cycle, as is conventional. In this mode of operation, the aperture of port 16 is constant. Due to the differential in cross-sectional area between a relatively small piece of vitreous tissue 86 and fully open port 16, vacuum source 60 does not always efficiently aspirate tissue 86. However, as shown in FIG. 9, inner cutting member 14 of probe 10 is actuated from an open position A' of port 16, to a fully closed port position B, and back to position A', according to the preferred method of the present invention. In this mode of operation, the aperture of port 16 can be varied, for example to position A', according to the size of vitreous tissue 86. The similar cross-sectional areas of vitreous tissue 86 and open port 16 allow for higher effective vacuum pressure from vacuum source 60 and a more efficient aspiration of tissue 86 into port 16. The concepts of dynamically varying the duty cycle and/or the open port size with cut rate according to the preferred methods of the present invention, and their resulting benefits, will now be discussed in more detail in connection with FIGS. 10, 11, and 12.

Figure 10:
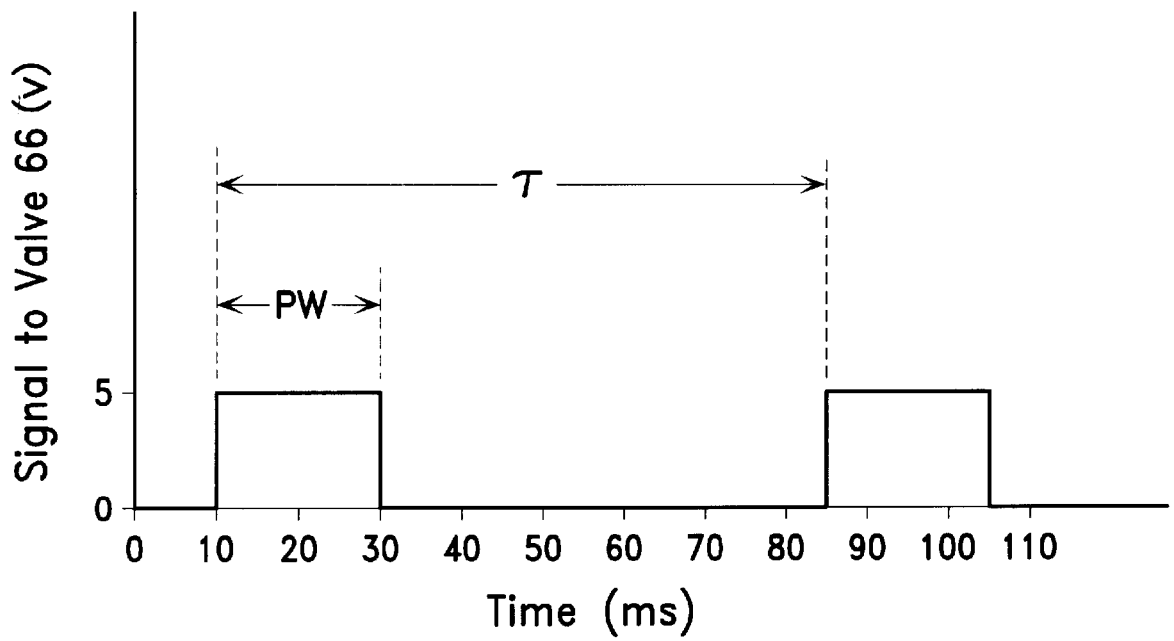
FIG. 10 is an exemplary electrical signal diagram for creating a pneumatic waveform for conventional operation of the probe of FIG. 1.

FIG. 10 shows an exemplary electrical signal supplied by microcontroller 54a to solenoid valve 66 so as to actuate inner cutting member 14 of probe 10 via pneumatic pressure source 58 and tubing 62. The closed position of valve 66 is preferably assigned a value of 0 volts, and the open position of valve 66 is preferably assigned a value of 5 volts. For a given cut rate, probe 10 will have a period τ representative of the time to open valve 66, plus the time valve 66 is held open, plus the time to close valve 66, plus the time valve 66 is held closed until the next signal to open valve 66 occurs. τ is the inverse of cut rate. For example, at a cut rate of 800 cpm, τ=75 milliseconds (ms)/cut. For the purposes of this document, the duration of the electrical signal that holds valve 66 in the open position is defined as the pulse width PW. As used in this document, port open duty cycle, or duty cycle, is defined as the ratio of PW to $\tau$ (PW/$\tau$).

Figure 11:
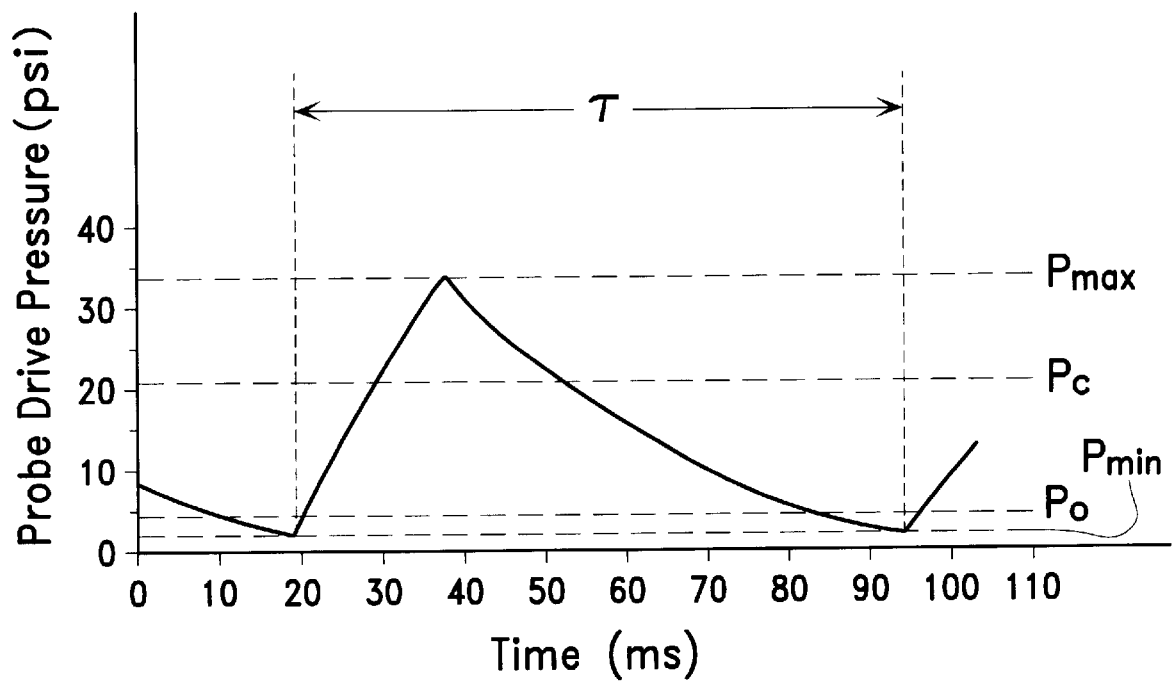
FIG. 11 is an exemplary pneumatic waveform for conventional operation of the probe of FIG. 1.

As shown in FIG. 11, $\tau$ also represents the time between respective pneumatic pulses generated by air/fluid module 56 in response to the electrical signal of FIG. 10. The pneumatic signal lags the electrical signal at valve 66 by approximately 9 ms (about 2 ms of delay in opening valve 66 and about 7 ms of transmission delay along PVC tubing 62). It has been discovered that an exemplary pneumatic/mechanical spring actuated probe 10, the Accurus® probe available from Alcon Laboratories, Inc. of Fort Worth, Tex., is at the fully closed port position B at a pressure Pc of about 21 psi, and is at the fully open port position B at a pressure Po of about 4 psi. This exemplary probe is driven by air/fluid module 56 with pressure pulses having a maximum pressure Pmax of about 34 psi and a minimum pressure Pmin of about 3 psi. Pc, Po, Pmax, and Pmin may vary for different probes.

As mentioned above, the cut rate of probe 10 or cycling rate of the electrical signal at valve 66 is equal to 1/$\tau$. Thus, increased cut rate results in decreased period $\tau$. If PW is held constant, this decrease in $\tau$ results in an increase in duty cycle, which causes the DC or bias level of the pneumatic waveform in FIG. 11 to shift upwards. Independent of PW, increased cut rate gives rise to reduced peak-peak pneumatic excursion between Pmax and Pmin.

The motion of inner cutting member 14 is directly related to the pressure applied to drive probe 10. Combining this understanding with the previously described effects of PW and cut rate on the pneumatic signal, an increase in cut rate with PW held constant 0 has the net effect of creating inner cutting member 14 motion that is both reduced in amplitude and shifted in the direction of port closure (i.e., toward line B of FIG. 2).

FIG. 11 also shows excess pneumatic drive of Pmax beyond Pc, which provides for probe 10 actuation variations as well as minor tolerances in other system components, including valve 66, PVC tubing 62, and pressure source 58. By reducing these variations and tolerances, much of the excess time and pressure in establishing Pmax is eliminated. In other words, if Pmax is set to Pc, cutting edge 20 of inner cutting member 14 is actuated just past cutting edge 18 of outer cutting member 12 and no more. The time for the pneumatic drive of probe 10 to return to Po is also reduced, thereby allowing for further reduction in period $\tau$ and, therefore, a further increase in cut rate.

Figure 12:
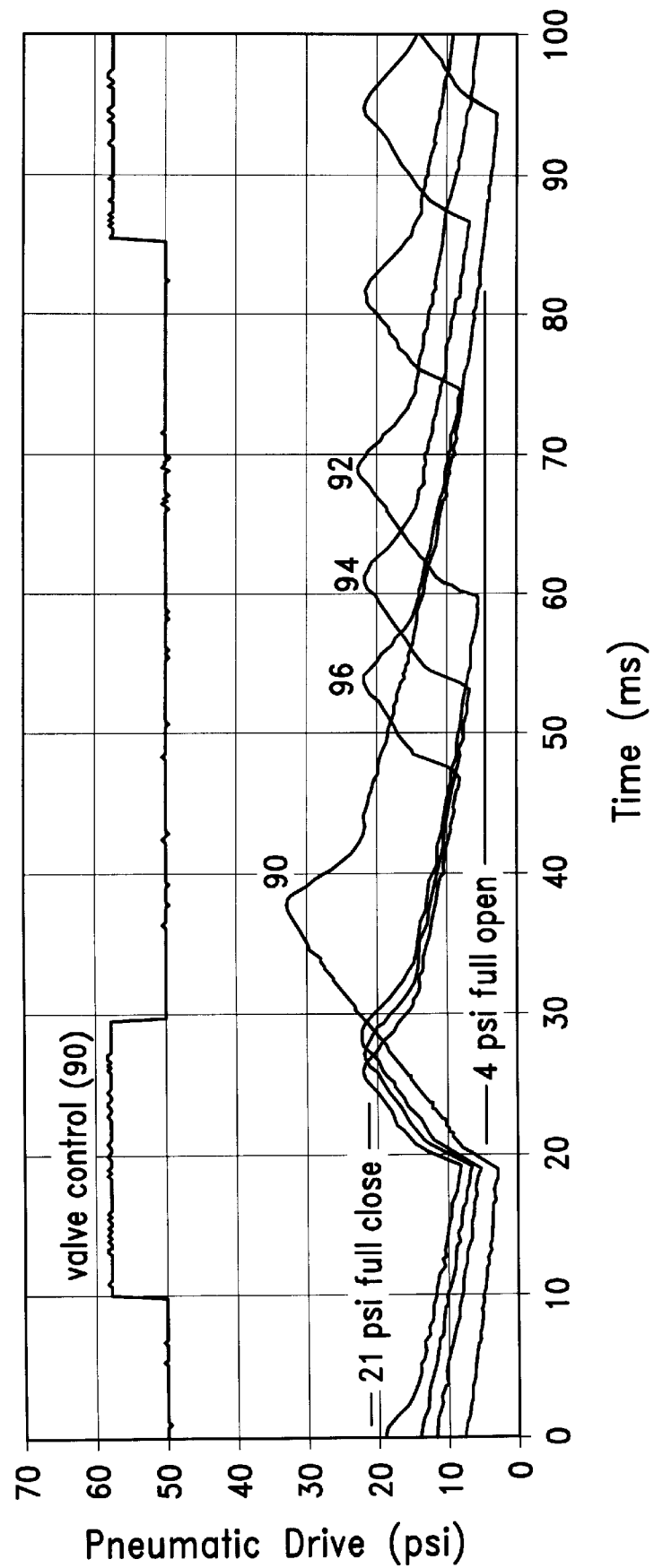
FIG. 12 shows a collection of pneumatic waveforms for operation of the probe of FIG. 1 according to a preferred method of the present invention.

FIG. 12 shows a collection of pneumatic waveforms as measured for a pneumatic/mechanical spring actuated probe 10. Waveform 90 represents the pneumatic drive that is conventionally applied at probe 10, and waveforms 92, 94, and 96 represent examples of pneumatic drive applied according to a preferred method of the present invention. Pressure levels of Pc=21 psi for full port closure and Po=4 psi for full port open are indicated. The electrical signal at valve 66 for conventional waveform 90 is shown at top. The 9 ms delay from electrical signal 90 for pneumatic waveform 90 is also indicated.

Waveform 90 depicts the conventional 800 cpm pneumatic drive for probe 10. In this case, inner cutting member 14 travels past each end of port 16 as Pmax=34 psi and Pmin=3 psi provide for full excursion. In contrast, waveforms 92, 94, and 96 yield inner cutting member 14 travel that extends to cutting edge 18 but which do not result in a fully open port 16. More specifically, waveform 92 yields a 75% open port 16 in each cut cycle, waveform 94 yields a 50% open port 16 in each cut cycle, and waveform 96 yields a 25% open port 16 in each cut cycle. For these waveforms, each cut rate is established for the desired range of inner cutting member 14 excursion, and then pulse width PW is increased or decreased as required to establish Pmax substantially equal to Pc for inner cutting member 14 travel just past cutting edge 18. This adjustment of pulse width PW also varies the duty cycle (PW/$\tau$).

Referring again to flow profile 80 of FIG. 7, pulse width PW is preferably lower at higher cut rates (e.g. above 800 cpm) than at lower cut rates (e.g. below 800 cpm). The lower pulse width PW at higher cut rates allows probe 10 to be operated with sufficient flow through port 16 at cut rates above the conventional range. Lowering pulse width PW at higher cut rates also results in the duty cycle being lower that it would have been if PW had been held constant. By varying pulse width PW or duty cycle, the flow rate through port 16 can be varied to any desired amount.

At lower cut rates, inner cutting member 14 preferably moves from a fully open position of port 16, to a fully closed position of port 16, and back to a fully open port position in each cut cycle. After a certain threshold cut rate, the open port size of port 16 preferably begins to decrease with increasing cut rate. By varying pulse width PW or duty cycle as described above, any desired amount of port open size or port aperture may be established. The threshold cut rate at which the open port size of port 16 begins to decrease may vary for different probes.

For each incremental cut rate on flow profile 80, the cut rate and the pulse width PW (or duty cycle PW/$\tau$) corresponding to the cut rate are preferably associated with a position on variable controller 68. This association is preferably made by software and/or hardware resident in microcomputer 52 or microcontroller 54$a$.

Variable controller 68 is preferably a conventional foot pedal having a range of motion in a generally vertical plane. The highest value of cut rate (and thus the lowest value of flow rate and the smallest aperture of port 16) is preferably assigned to the uppermost position of foot pedal 68. Decreasing values of cut rate are preferably assigned to increasingly depressed positions on foot pedal 68. The lowest value of cut rate (and thus the highest value of flow rate and a fully open aperture of port 16) is preferably assigned to the fully depressed position of foot pedal 68. Therefore, before a surgeon depresses foot pedal 68, probe 10 operates in the highest cut rate, smallest port aperture, and lowest flow rate mode. This mode of operation is especially useful for performing delicate operations near the retina, such as mobile tissue management, vitreous base dissection, or membrane removal. As the surgeon depresses foot pedal 68, the cut rate decreases and the flow rate increases, according to flow profile 80 of FIG. 7, until the lowest cut rate, fully open port aperture, and highest flow rate is reached. This lower cut rate mode of operation is especially useful for core vitrectomy or the removal of large vitreous tissue such as traction bands. Alternatively, an opposite procedure may be followed so that before a surgeon depresses foot pedal 68, probe 10 operates in the lowest cut rate, fully open port aperture, highest flow rate mode. As the surgeon depresses foot pedal 68, the cut rate increases and the flow rate decreases, according to flow profile 80 of FIG. 7, until the highest cut rate, smallest port aperture, and lowest flow rate is reached.

Although the method of dynamically varying the port open duty cycle and/or port aperture has been described above with reference to a pneumatic/mechanical spring actuated probe 10, it will be apparent to one skilled in the art that it is equally applicable to a dual pneumatically actuated probe 30. In addition, it is believed that duty cycle and/or port aperture can also be varied so as to extend the range of flow and cut rates for a probe that is actuated using a conventional linear electrical motor, solenoid, or other electromechanical apparatus.

From the above, it may be appreciated that the present invention provides an improved method of performing all of the fundamental aspects of vitrectomy surgery that provides significant benefits to both the surgeon and the patient. The present invention is illustrated herein by example, and various modifications may be made by a person of ordinary skill in the art. For example, although the methods of dynamically varying the port open duty cycle and/or port aperture with cut rate are described above in connection with the operation of vitrectomy probes, the methods are equally applicable to the operation of microsurgical aspiration probes, or other microsurgical probes used to cut and remove body tissue in a similar manner. Of course, in an aspiration probe the inner cutting member would be replaced with a sealing member, and cycle rate would replace cut rate. As another example, although the preferred flow profile of the present invention is substantially linear, the method of the present invention is equally applicable to non-linear flow profiles. As another example, although the preferred flow profile of the present invention is illustrated using an exemplary aspiration of 150 mmHg vacuum, the method of the present invention is equally applicable to flow profiles at different levels of aspiration. As a further example, alternative techniques may be used to control flow rate, other than by adjusting cut rate, duty cycle, and pulse width as described hereinabove in connection with probe 10.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A method of operating a vitrectomy probe, said probe comprising a port for receiving tissue and an inner cutting member, comprising the steps of:

providing a foot pedal having a generally vertical range of motion;

providing a vacuum source;

fluidly coupling said vacuum source to said probe;

inducing a flow of said tissue into said port with said vacuum source; and actuating, in response to a movement of said foot pedal, said inner cutting member in a cyclic manner to open and close said port over a plurality of cut rates, wherein said cut rate is at a highest value and an open size of said port is at a smallest value when said foot pedal is in a fully undepressed position, said cut rate is at a lowest value and said open size of said port is at a largest value when said foot pedal is in a fully depressed position, moving said foot pedal in a downward direction decreases said cut rate and increases said open size of said port, and moving said foot pedal in an upward direction increases said cut rate and decreases said open size of said port.

* * * * *